(12) United States Patent
Curran et al.

(10) Patent No.: US 12,138,491 B2
(45) Date of Patent: Nov. 12, 2024

(54) POWERED EXHAUST APPARATUS FOR A PERSONAL PROTECTION RESPIRATORY DEVICE

(71) Applicant: 3M INNOVATIVE PROPERTIES COMPANY, St. Paul, MN (US)

(72) Inventors: Desmon T. Curran, Durham (GB); John A. Duff, London (GB); Benjamin H. Cooper, Bishop Auckland (GB); Jason A. Graves, Darlington (GB); Reyad A. Abdulqader, Stockton-On-Tees (GB)

(73) Assignee: 3M Innovative Properties Company, St. Paul, MN (US)

( * ) Notice: Subject to any disclaimer, the term of this patent is extended or adjusted under 35 U.S.C. 154(b) by 180 days.

(21) Appl. No.: 17/651,605

(22) Filed: Feb. 18, 2022

(65) Prior Publication Data
US 2022/0168597 A1 Jun. 2, 2022

Related U.S. Application Data

(63) Continuation of application No. 15/740,134, filed as application No. PCT/US2016/039732 on Jun. 28, 2016, now abandoned.

(30) Foreign Application Priority Data

Jul. 7, 2015 (GB) ...................................... 1511904

(51) Int. Cl.
*A62B 18/00* (2006.01)
*A61M 16/00* (2006.01)
(Continued)

(52) U.S. Cl.
CPC ....... *A62B 18/006* (2013.01); *A61M 16/0066* (2013.01); *A61M 16/106* (2014.02);
(Continued)

(58) Field of Classification Search
CPC ....... A62B 18/10; A62B 18/02; A62B 18/025; A62B 18/006
See application file for complete search history.

(56) References Cited

U.S. PATENT DOCUMENTS

| 5,413,097 A * | 5/1995 | Birenheide ............... A62B 7/10 128/206.17 |
| 2005/0103343 A1 * | 5/2005 | Gosweiler ............ A62B 18/006 128/205.12 |

(Continued)

FOREIGN PATENT DOCUMENTS

| CN | 104548406 | 4/2015 |
| CN | 104667401 | 6/2015 |

(Continued)

OTHER PUBLICATIONS

International Search Report for PCT International Application No. PCT/US2016/039732, mailed on Sep. 1, 2016, 4pgs.

*Primary Examiner* — Bradley H Philips
*Assistant Examiner* — Savannah L Gabriel

(57) ABSTRACT

An exhaust apparatus for connection to a personal protection respiratory device that defines a filtered air volume adjacent to the face of a wearer and comprises at least one exhalation, the apparatus comprising a blower in fluid connection with the at least one exhalation valve, the blower being responsive to the wearer's respiratory cycle to draw a substantial portion of the wearer's exhaled breath through the at least one exhalation valve wherein, in response to the wearer's respiratory cycle, the blower operates throughout the wearer's exhale breath, or a substantial period thereof, and does not operate throughout the wearer's inhale breath, or a substantial period thereof

16 Claims, 7 Drawing Sheets

(51) Int. Cl.
*A61M 16/10* (2006.01)
*A62B 9/02* (2006.01)
*A62B 18/10* (2006.01)
*A62B 23/02* (2006.01)
*A62B 7/10* (2006.01)
*A62B 18/02* (2006.01)

(52) U.S. Cl.
CPC ............... *A62B 9/02* (2013.01); *A62B 18/10* (2013.01); *A62B 23/025* (2013.01); *A61M 2205/8206* (2013.01); *A62B 7/10* (2013.01); *A62B 18/02* (2013.01)

(56) References Cited

U.S. PATENT DOCUMENTS

| | | | | |
|---|---|---|---|---|
| 2008/0035150 | A1* | 2/2008 | Rittner | .................... A62B 18/10 |
| | | | | 128/205.25 |
| 2012/0174922 | A1* | 7/2012 | Virr | ..................... A61M 16/106 |
| | | | | 128/206.28 |
| 2013/0098359 | A1* | 4/2013 | Becker | .............. A61M 16/0683 |
| | | | | 128/201.13 |
| 2016/0310769 | A1 | 10/2016 | Tang et al. | |

FOREIGN PATENT DOCUMENTS

| | | | | |
|---|---|---|---|---|
| CN | 105982378 | | 10/2018 | |
| EP | 0094757 | | 11/1983 | |
| EP | 0334555 | A2 | 9/1989 | |
| KR | 20100003793 | U | 4/2010 | |
| WO | WO 2013/039153 | | 3/2013 | |
| WO | WO 2014/035641 | | 3/2014 | |
| WO | WO-2014035641 | A2 * | 3/2014 | ........ A61M 16/0066 |
| WO | WO 2014/081788 | | 5/2014 | |

\* cited by examiner

POWERED EXHAUST APPARATUS FOR A PERSONAL PROTECTION RESPIRATORY DEVICE

CROSS REFERENCE TO RELATED APPLICATIONS

This application is continuation of U.S. Ser. No. 15/740,134, filed Dec. 27, 2017, now pending, which is a national stage filing under 35 U.S.C. 371 of PCT/US2016/039732, filed Jun. 28, 2016, which claims the benefit of Great Britain Application No. 1511904.3, filed Jul. 7, 2015, the disclosure of which is incorporated by reference in its/their entirety herein.

TECHNICAL FIELD OF THE INVENTION

The present invention relates to an exhaust apparatus for personal protection respiratory devices, particularly, but not exclusively to negative pressure respirators. In particular, the present invention relates to a powered exhaust apparatus which can be connected, either permanently or releasably, to a personal protection respiratory device. In use, the powered exhaust apparatus removes the hot and moist air that can often build-up inside a negative pressure respirator to significantly improve and enhance wearer comfort, whilst maximizing filter life and minimizing respiratory effort.

BACKGROUND

Negative pressure respirators are well known in the art. With respirators of this type, filtered air is drawn into the enclosed space between the inside of the respirator and a wearer's face through a filter system by the wearer's breathing action. When the wearer draws a breath, negative pressure is created in the respirator and air is drawn in through the filter system. When the wearer exhales a breath, spent air leaves the respirator through an exhalation valve and/or back through the filter system.

Although negative pressure respirators are available in many different configurations, and offer many different benefits, they all have one major drawback, that of the uncomfortable build-up of heat and moisture that can sometimes occur inside the respirator. The heat and moisture build-up is caused by the trapping of the wearer's exhaled breath in the cavity created between the respirator and the wearer's face. As the wearer works harder, and/or wears the respirator for extended periods of time, heat and moisture build-up may increase.

Many different solutions have been proposed in the prior art to eliminate, or at least minimise, the problem of heat and moisture build-up inside negative pressure respirators. For example, the addition of exhalation valves, and optimising the operation of these exhalation valves. The design and optimisation of low pressure drop filters and media has also been proposed to alleviate this problem and/or by controlling the filter surface area and filter material pressure drop. Another solution in the prior art is to include pads to absorb the moisture.

A further solution is offered in WO2014/081788 in which a respirator has a blower in fluid connection with the exhalation valve, the blower being operable to draw the wearer's exhaled breath through the valve. This solution presents advantages but also has drawbacks in that the blower applies a constant negative pressure to the exhale valve. This can lead to increased inhalation effort and decreased filter life as a result of the increased flow of air passing through the filter.

It is therefore an object of the invention to deliver the improved cooling effects of the prior art device whilst not unduly reducing filter life or increasing inhalation effort.

Accordingly, a first aspect of the present invention provides an exhaust apparatus for connection to a personal protection respiratory device that defines a filtered air volume adjacent to the face of a wearer and comprises at least one exhalation valve, the apparatus comprising:

a blower in fluid connection with the at least one exhalation valve, the blower being responsive to the wearer's respiratory cycle to draw a substantial portion of the wearer's exhaled breath through the at least one exhalation valve, wherein, in response to the wearer's respiratory cycle, the blower operates throughout the wearer's exhale breath, or a substantial period thereof, and does not operate throughout the wearer's inhale breath, or a substantial period thereof.

Operating the blower substantially only during the exhale portion of the wearer's respiratory cycle (or a substantial part thereof) delivers significant advantages to the present invention as follows.

Firstly, the volume of air drawn through the filter is reduced. In the prior art device the volume of air drawn through the filter media during inhalation was increased under the action of the blower since both the lungs and the blower were drawing air in through the filter. This is not the case in the present invention. This reduces the load on the filter media and thereby increases the life of the filter under a given load.

Secondly, the power consumed by the blower is significantly reduced by only operating during the exhale breath, or substantially only during the exhale breath. This in turn reduces the size of the battery for a given operating life which reduces the weight of the device. Weight reduction brings improvements in the perceived comfort of the respirator.

Thirdly, inhalation effort of the wearer is reduced since the wearer no longer has to overcome the pressure drop generated by the blower before the inhalation breath starts to deliver air to the lung cavity. This in turn further assists in reducing the temperature and humidity in the respirator through reduced respiratory load on the wearer.

Preferably, the exhaust apparatus further comprises
a controller,
a pressure sensor for sensing a pressure generated by the wearer's breathing cycle and sending a pressure signal indicative of the pressure to the controller,
the controller being in communication with the pressure sensor and the blower,
wherein the controller operates the blower in response to the pressure signal.

Preferably, the pressure is sensed in a filtered air volume of the personal protection respiratory device.

Alternatively, the pressure is sensed downstream of the exhalation valve.

Alternatively, the pressure is sensed upstream of the inhalation valve

Preferably, the controller starts the blower when the pressure sensed by the pressure sensor reaches a first predetermined pressure.

Preferably, the controller stops the blower when the pressure sensed by the pressure sensor falls below a second predetermined pressure.

Preferably, the first predetermined pressure and the second predetermined pressure are a common predetermined pressure.

Preferably, the common predetermined pressure is substantially ambient pressure so that the controller starts the blower substantially at the initiation of the wearer's exhale breath and stops the blower substantially at the end of the wearer's exhale breath.

Alternatively, the common predetermined pressure is higher than ambient pressure so that the controller starts the blower momentarily after the initiation of the wearer's exhale breath and stops the blower momentarily before the end of the wearer's exhale breath.

Alternatively, the common predetermined pressure is lower than ambient pressure so that the controller starts the blower momentarily before the initiation of the wearer's exhale breath and stops the blower momentarily after the end of the wearer's exhale breath.

Alternatively, the first predetermined pressure is greater than the second predetermined pressure so that the controller starts the blower momentarily after the initiation of the wearer's exhale breath and stops the blower momentarily after the end of the wearer's exhale breath.

Alternatively, the second predetermined pressure is greater than the first predetermined pressure so that the controller starts the blower momentarily before the initiation of the wearer's exhale breath and stops the blower momentarily before the end of the wearer's exhale breath.

Preferably, the blower further comprises an inlet, a motor, a fan, and an outlet.

Preferably, the exhaust apparatus further comprises an attachment means for releasably connecting the blower to the at least one exhalation valve.

Preferably, the exhaust apparatus is generally L-shaped comprising an upwardly extending portion and rearwardly extending portion.

Preferably, the rearwardly extending portion houses a battery for powering the blower.

Preferably, the personal protection respiratory device is selected from a group consisting of disposable, reusable, half mask, full face, particulate, gas and vapour and tight-fitting hood respirators.

A second aspect of the present invention provides a method of controlling the exhaust apparatus of any preceding claim, including the steps of:
setting a predetermined pressure,
starting the blower when the pressure sensed by the pressure sensor reaches the predetermined pressure,
stopping the blower when the pressure sensed by the pressure sensor falls below the predetermined pressure.

BRIEF DESCRIPTION OF THE DRAWINGS

The present invention will now be described by way of example only, and with reference to the accompanying drawings, in which.

DETAILED DESCRIPTION OF THE PREFERRED EMBODIMENTS

Figure 1:
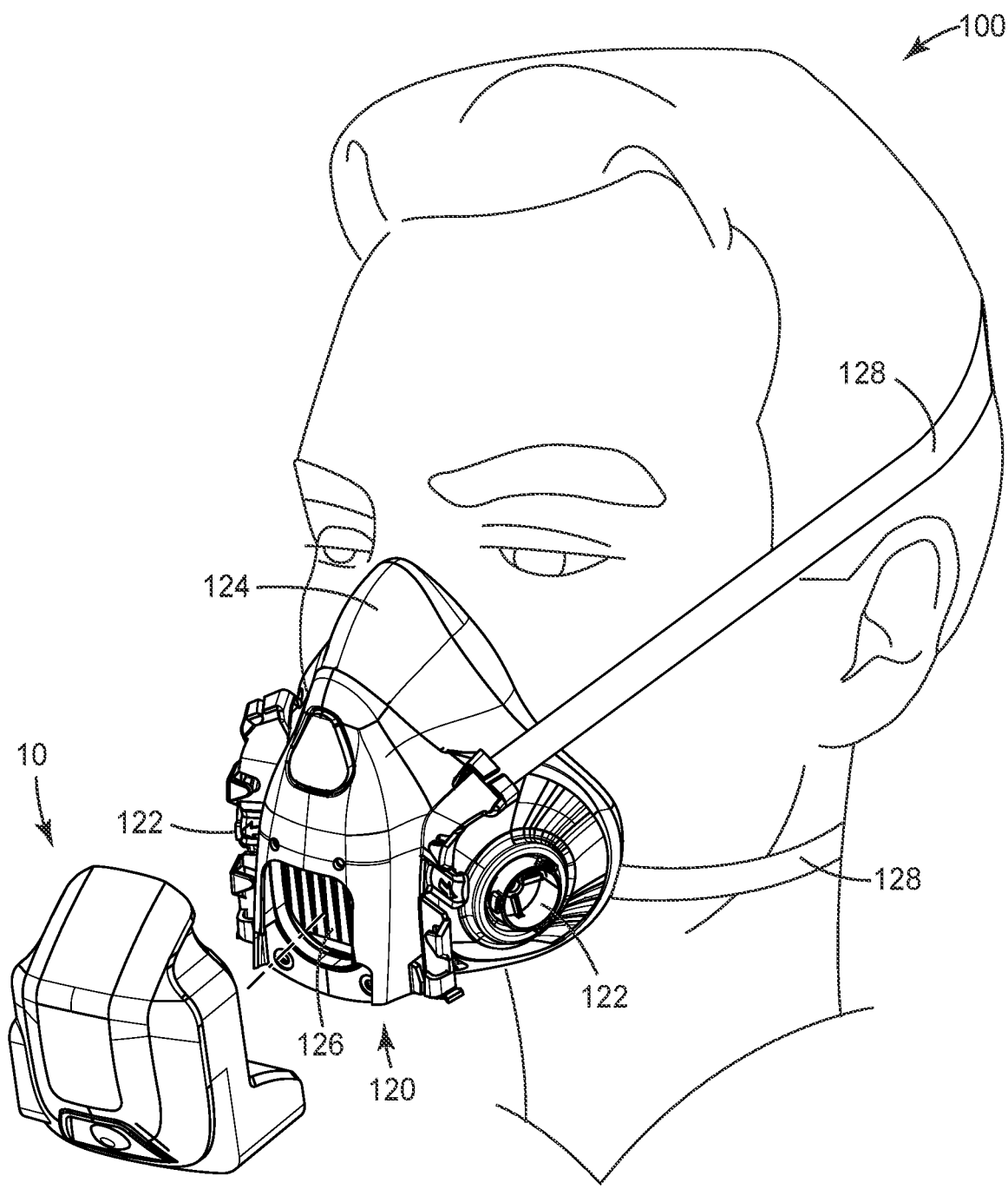
FIG. 1 is an exploded front side perspective view of an exhaust apparatus according to the present invention for connection to a personal protection respiratory device.

FIG. 1 is an exploded view of an exhaust apparatus according to the present invention indicated generally at 10. The apparatus 10 is able to connect or otherwise engage to or with a personal protection respiratory device 120, either in a permanent fashion or in a releasable manner as will be described in further detail shortly.

Whilst the respirator 120 illustrated in FIGS. 1, 2, 5, and 7 is indicative of the 3M™ 7500 Series of gas, vapour and particulate respirators, the exhaust apparatus 10 of the present invention can be utilised with any negative pressure respiratory device 120. The skilled person will appreciate that the term "respirator" or "respiratory mask", as used interchangeably herein, is intended to mean a breathing device worn to prevent the inhalation of hazardous substances, particles, vapours or noxious gases. The term "negative pressure respiratory mask" is intended to cover any respirator in which the air pressure inside the mask becomes lower than the ambient air pressure when the wearer inhales.

A negative pressure respiratory mask 120 as described herein is used to mean any form of respirator intended to fit the face of the wearer 100 in a substantially sealed configuration causing the air inhaled and exhaled by the wearer 100 to pass through a filter body or a filter portion of the respirator or exhalation valve). Negative pressure respiratory mask 120 can be full or half facepiece mask, depending upon the hazard of concern. Again, these masks utilise a filter which prevents the inhalation of contaminants, particles, gases and vapours from the air inhaled by the wearer. Some common examples of this type of respirator are manufactured by 3M Company located in St. Paul, Minnesota, and include the 3M™ 4000, 6000 and 6500 Series of reusable respirators or tight-fitting hood facepiece respirators.

Disposable respirators, such as the 3M™ 8000 and 9000 Series of cup-shaped and flat-folded products, are lightweight single-piece respirators that employ a filter media which removes particulates and mists from the air stream as the wearer draws a breath. The entire unit is designed to be discarded after some extended period or a single use or single shift, depending on the contaminant. Filtering facepieces, such as the 3M™ 4000, 6000 and 6500 Series are generally reusable products and which can have replaceable filter cartridges. Typically one or two cartridges attach securely to half mask or full facepiece which has built into it a corresponding number of valves for inhalation, and usually one for exhalation.

The personal protection respiratory device 20 that is illustrated in FIG. 1 is a 3M™ 7500 half mask to which filters can be attached using bayonet connectors.

Figure 2:
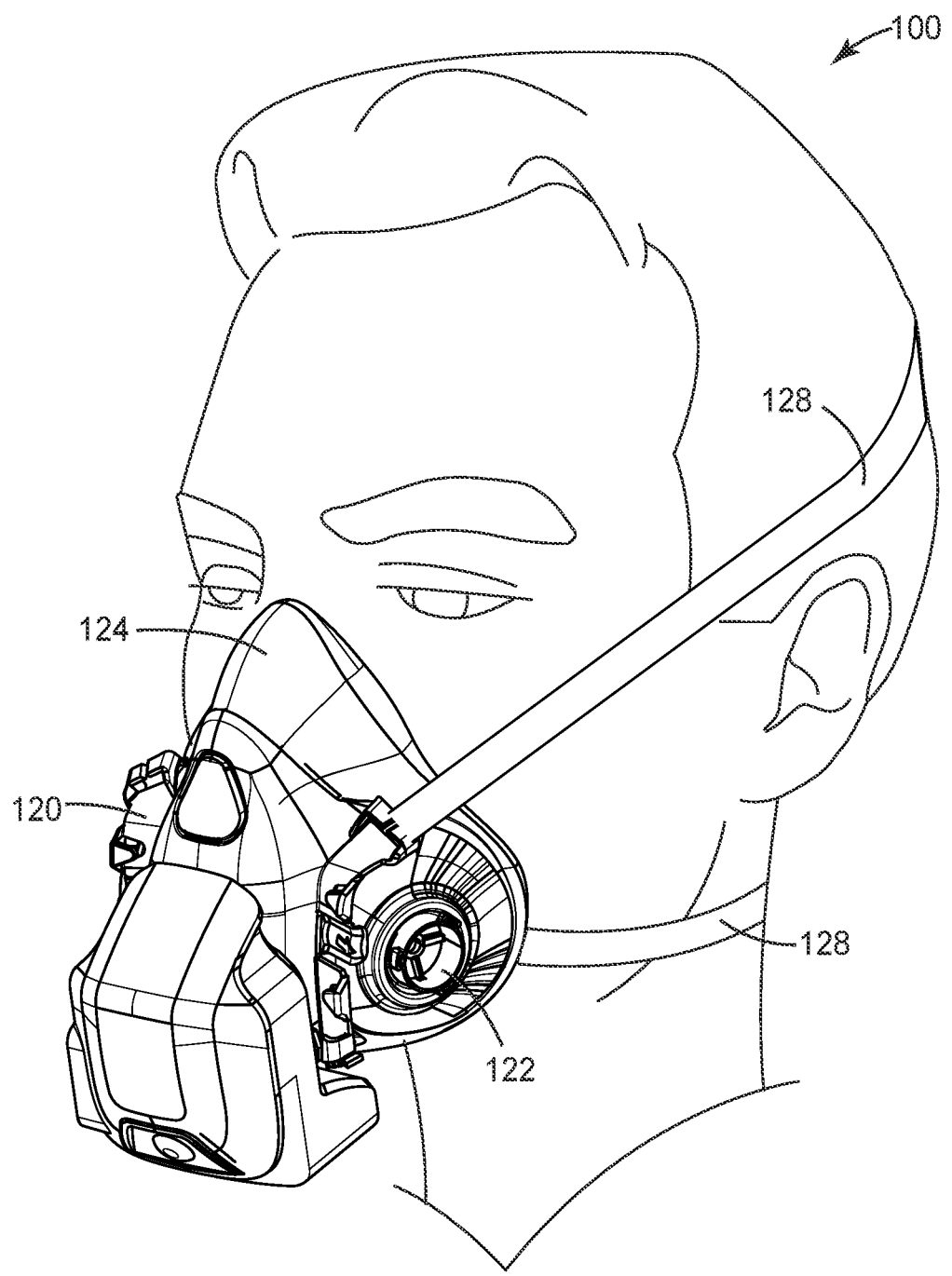
FIG. 2 is a front side perspective view of the exhaust apparatus of FIG. 1 connected to the personal protection respiratory device 2.

Referring to FIGS. 1 and 2, a pair of filter cartridges (not shown for clarity) are attached to the respirator mask 120 at respective inhalation ports 122. Each of the inhalation ports 122 has a respective inhalation valve 136 (shown in FIG. 7) on the inside of the respirator mask 120 which open as a wearer 100 draws a breath. The face mask 120 has an exhalation valve 126 with a one-way exhalation valve diaphragm 138 (shown in FIG. 7) which open as a wearer 100 expels a breath. The mask 120 is held in position on the wearer's head by adjustable straps 128 (shown only in FIGS. 1 and 2).

The respiratory mask 120 has a conformable gasket or seal 124 which generally encloses the wearer's 100 mouth and nose. Since a good seal is needed to ensure filtration of the containments, one drawback in the prior art is that sometimes an uncomfortable build-up of heat and moisture is noticed by the wearer 100 inside the respirator 120. As the wearer 100 works harder, and or wears the respirator 120 for extended periods of time, heat and moisture build-up can occur. The heat and moisture build-up is caused by the trapping of the exhaled breath in the cavity created between the respirator 120 and the wearer's 100 face.

Figure 3:
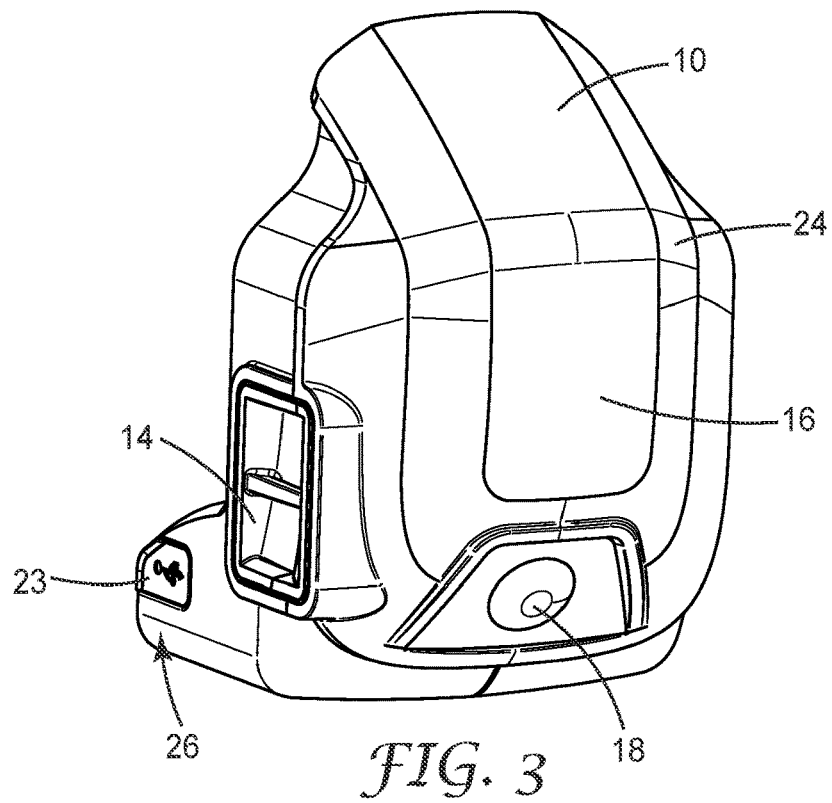
FIG. 3 is a front side perspective view of the exhaust apparatus of FIG. 1.
Figure 4:
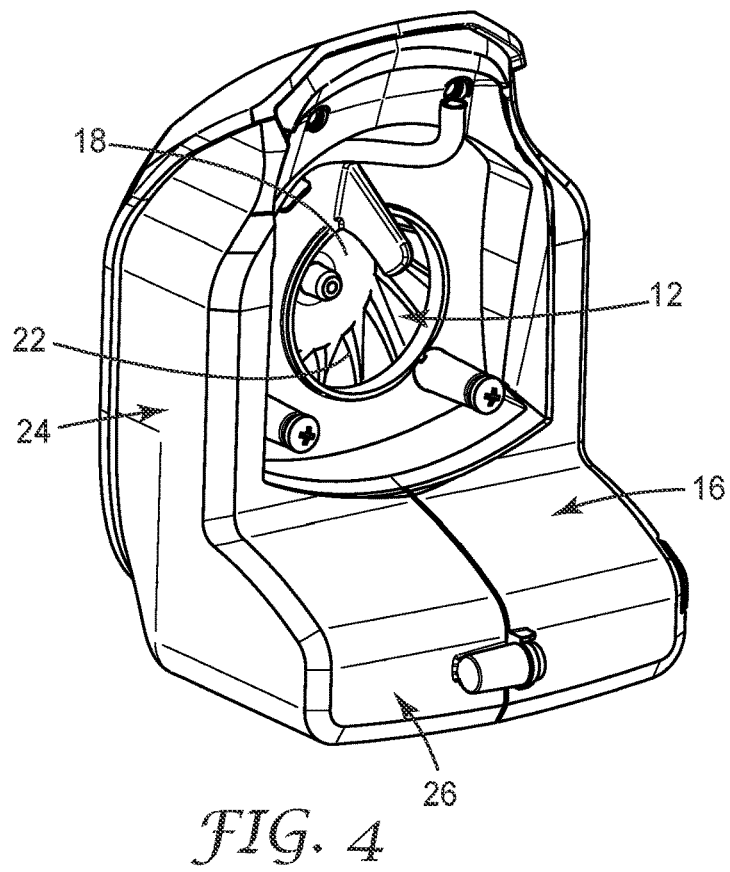
FIG. 4 is a rear side perspective view of an exhaust apparatus of FIG. 1.

As illustrated in FIGS. 1 and 2, and in further detail in FIGS. 3 and 4, the present invention defines an exhaust apparatus 10 having a housing 16 with a generally L-shaped form. The exhaust apparatus 10 includes an inlet 12 (see FIG. 4) and an outlet 14 (see FIG. 3). The outlet 14 is formed in a side surface of the housing 16. Positioned inside housing 16 between the inlet 12 and the outlet 14 is a blower 18 which in use draws air out of the respiratory device 120. The blower 18 has a motor 20 which drives a fan 22. The motor 20 is powered by a battery 25, which will be described in further detail shortly with reference to FIG. 6.

The apparatus 10 has an upwardly extending section indicated generally at 24 which houses the inlet 12, outlet 14 and blower 18. The apparatus 10 has a rearwardly extending section indicated generally at 26 which houses the battery 25 and a controller 28 (shown in FIG. 6). The positioning of the battery 25 (a relatively heavy component of the device 10) in the rearwardly extending section 26 allows the centre of mass of the device to sit most closely to the centre of mass of the head. This improves the comfort of the apparatus by minimizing the moment of inertia of the device as the user 100 moves his or her head during use.

To operate the apparatus, a switch mechanism 18 is accessible to the wearer 100. The switch mechanism 18 can have a simple on/off mode of operation or can include a variable adjustment so that the wearer 100 can optimise the desired blower speed, and hence, cooling effect based upon the environmental conditions, the task the wearer 100 is undertaking, and the wearer's personal choice. Alternatively the settings may be preconfigured by connection to managing software on a PC via USB connection port 23. The connection port 23 also serves as a charging port for the battery 25.

In use a cooling effect is achieved by the exhaust apparatus 10 as follows. When the wearer 100 inhales a breath, "cooler" ambient air is drawn into the respiratory mask 20 either though the filter cartridges and inlet ports 122 as shown in FIGS. 1 and 2 in the case of a reusable mask, or through, for example, a filter portion or filtering mask body of the respirator, in the case of a disposable mask. Heat and moisture build-up is then caused by trapping the exhaled breath in the cavity created between the respirator 120 and the wearer's 100 face. When operated, the exhaust apparatus 10 of the present invention draws this warm and moist air out through the exhaust valve 126 during the exhale breath and reduces the exhalation breathing resistance, as described below. This produces a noticeable cooling benefit for the wearer 100 without placing a respiratory burden on the inhale breath or reducing the life of the filter.

Figure 5:
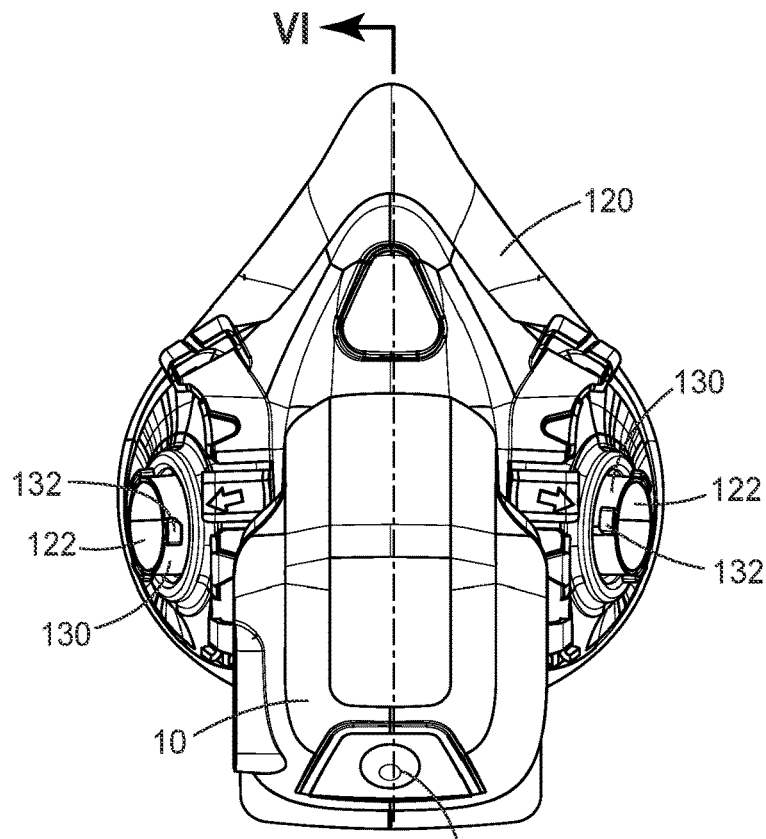
FIG. 5 is a front view of the exhaust apparatus of FIG. 1 connected to the personal protection respiratory device of FIG. 1.

Turning now to FIG. 5, the exhaust apparatus 10 is shown connected to the respirator 120. The mechanism for connection will be described in further detail below. FIG. 5 shows in greater detail the inlet ports 122 which are defined by port walls 130 which have bayonet fitting 132 of known design. The bayonet fittings 132 are provided to connect to the 3M™ 2000, 5000 or 6000 series of filters. However, it will be appreciated that alternative attachments mechanisms such as the DIN threaded filters may be provided in order to accept differing types of filters, Furthermore, an integral cartridge may be provided in line with the 3M™ 4000 series half masks without departure from the invention.

The inlet 12 of the exhaust device 10 is shaped to releasably connect by way of an interference fit to the shape and dimensions of the respective exhaust valve 126 situated on the respiratory mask 120. Whilst the exhaust apparatus 10 described herein in relation to FIG. 5 connects by way of an interference fit, the skilled person will appreciate that any form of releasable connection to the exhaust valve 126 is possible, including, for example, connection by way of a screw thread, snap fit engagement, bayonet, quick release mechanism etc. The above list is in no way intended to be limiting and exhaustive.

As an alternative to releasable connection described above, it may be desirable to utilize a direct permanent connection between the device 10 and the respiratory mask 120. Such connection might be by welding, adhesive or other known attachment mechanism such as attachment by screw as will be described in further detail shortly.

Figure 6:
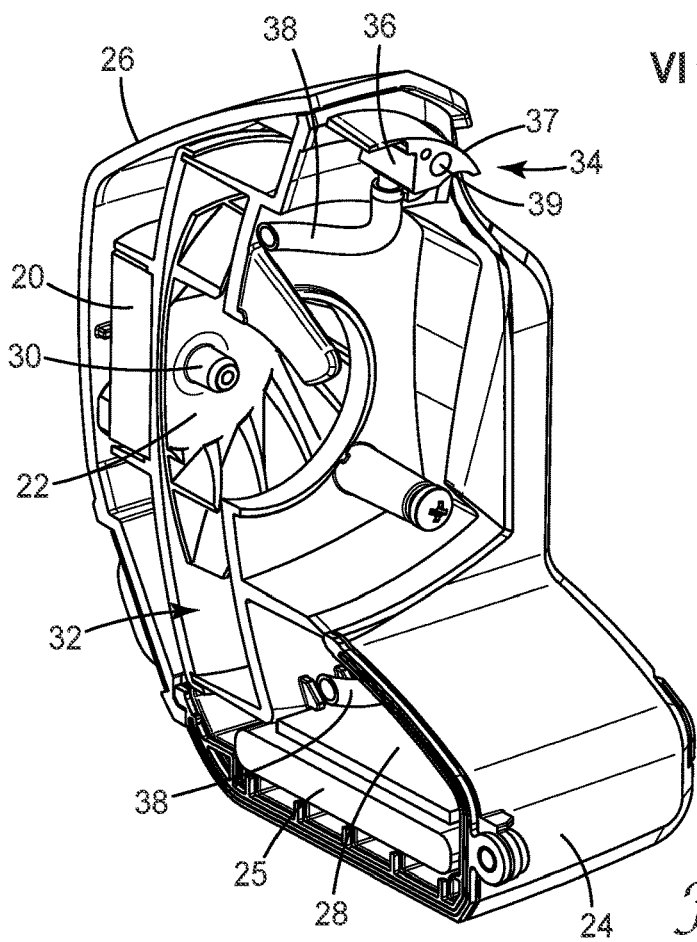
FIG. 6 is a cross-sectional rear side view of the exhaust apparatus of FIG. 1 taken along the dashed line VI-VI in FIG. 5.
Figure 7:
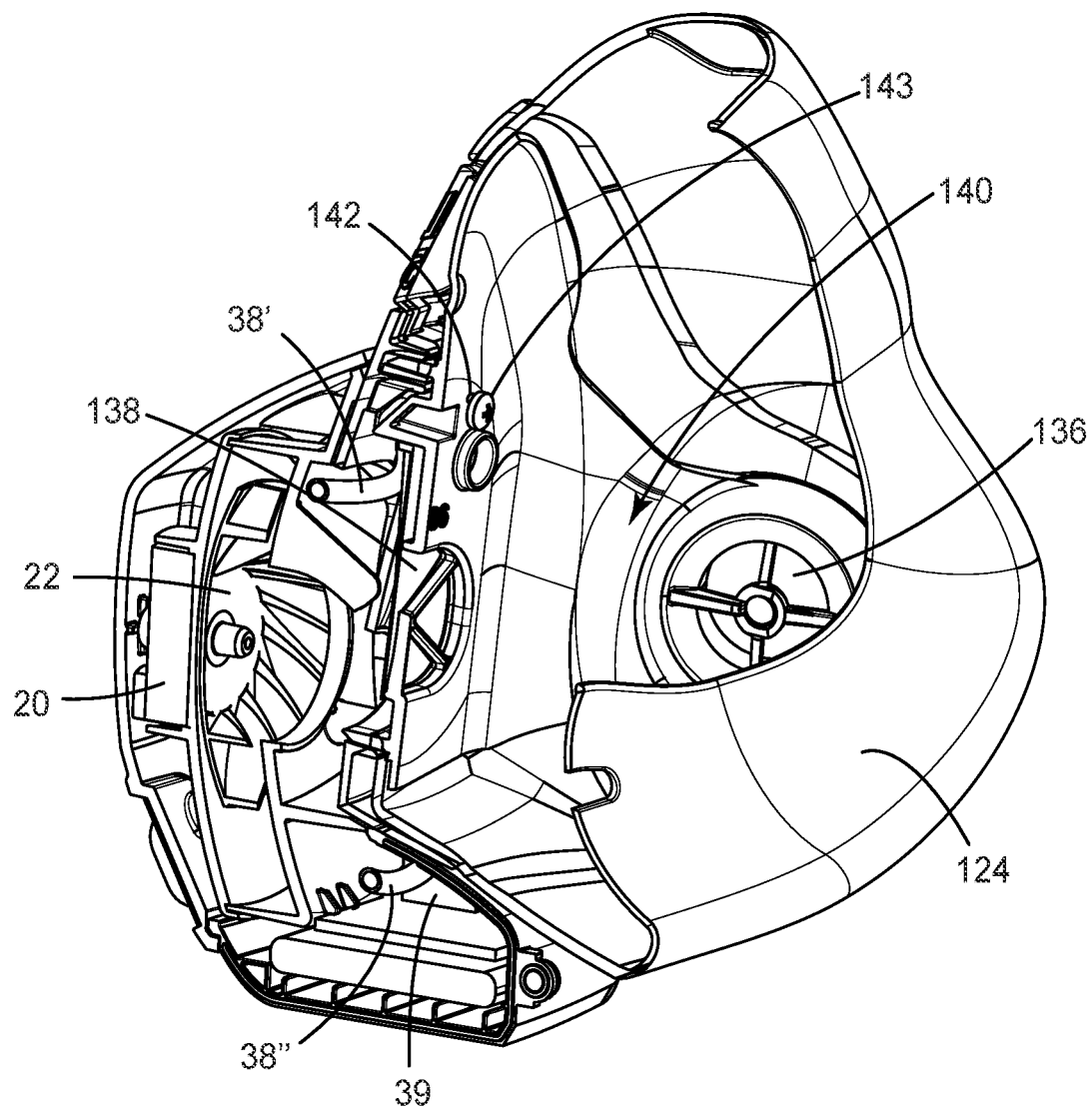
FIG. 7 is a cross-sectional rear side view of the exhaust apparatus of FIG. 1 connected to the personal protection respiratory device of FIG. 1 taken along the dashed line VI-VI in FIG. 5.

Referring now to FIGS. 6 and 7 the motor 20 is shown mounted within the upwardly extending section 26 of the exhaust apparatus 10. The motor 20 drives a shaft 30 which in turn drives the fan 22. When operative, the fan 22 draws air from the filtered air cavity (indicated generally at 140 in FIG. 7) of the respirator 120 past the valve 138 and expels the air through the fan scroll 32 which is connected to the outlet 14. In this way operation of the motor 20 is able to draw air from the cavity 140 and expel it to atmosphere. The motor 20 is powered by the battery 25 which is situated in the rearwardly extending section 26. Directly above the battery 25 is a controller 25 in the form of a microprocessor on PCB. The controller 28 is programmed to control the motor 20 is response to the wearer's breathing cycle.

The wearer's breathing cycle is detected by measuring the pressure of the filtered air volume in the filtered air cavity 140. This is achieved via a pressure port 142 (see FIG. 7) in the respirator 120. The pressure port 142 is in fluid communication with a pressure conduit 34 in the device 10. The pressure conduit is defined by a connector 36 and a pipe 38, the two ends of which 38', 38" are shown in FIG. 6. The connector 36 has an orifice 37 in fluid communication with the pressure port 142. The connector 36 seals against the forward face of the respirator 120 under the action of screw 143 (a second corresponding screw on the opposite side of the device 120 is not shown for clarity and by virtue of the cross-sectional view of FIG. 7) which passes through a hole 39 in the connector 36. The screw 143 also acts to supplement the interference fit between the exhaust apparatus 10 and the respirator 120 to mechanically attach the apparatus 10 to the device 120. The second end 38" of the pipe 38 is connected to a pressure transducer 39 (shown only in FIG. 7) which detects the pressure and sends a signal to the controller 28. It is conceivable within the scope of the application that the pressure generated by the wearer's breath could be measured at a position other than in the filtered air volume. For example the pressure could be detected downstream of the exhalation valve. This would remove the necessity for the connector 36 and pressure port 142 and their sealed interface. Alternatively the pressure could be sensed upstream of the inhalation valve at the inhalation ports 122.

Accordingly, the controller is able to continuously monitor the pressure in the cavity 140 and control the blower 18 via the motor 20 in order to ensure that the fan is, essentially, only operating during the exhale breath of the wearer 100. This operation will now be described in further detail.

Figure 8:
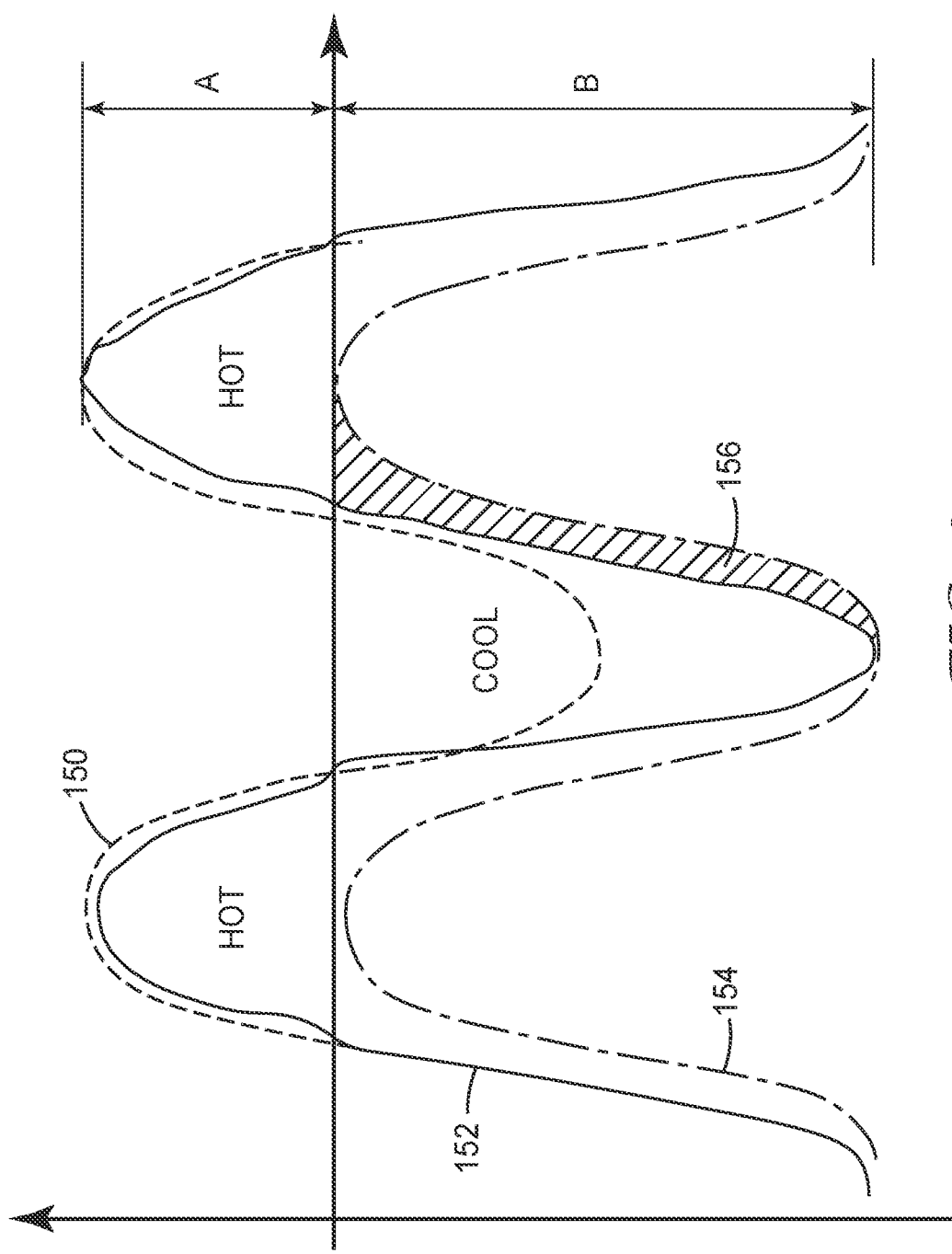
FIG. 8 is a chart illustrating the pressure and flow characteristics of the prior art device of WO2014/081788.

FIG. 8 shows a representation of pressure in, and flow rate through, the filtered air cavity in the prior art device of WO2014/081788. The dashed line 150 represents the flow rate through the mask and the solid line 152 represents the pressure in the mask cavity when the device is switched off. The flow rate naturally oscillates about zero as the wearer breaths in cool air through inhale breath B and breaths out hot air through exhale breath A. With the device switched on, the flow rate remains unchanged as the wearer continues to breathe the volume of air required to match respiratory demand. However, the pressure line drops to the extended dashed line 154 as the fan operates to maintain a negative pressure in the mask throughout both the inhale and exhale breath. This can only achieved by pulling additional air through the filters during the inhale stroke. This additional volume of air is driven by the additional negative pressure shown in the hatched area 156. The additional flow volume through the filter limits filter life. Furthermore, the additional negative pressure must be overcome by additional respiratory effort if the same flow rate is to be maintained. This additional respiratory effort may itself cause increased respiratory load resulting in an increased breathing rate.

Figure 9:
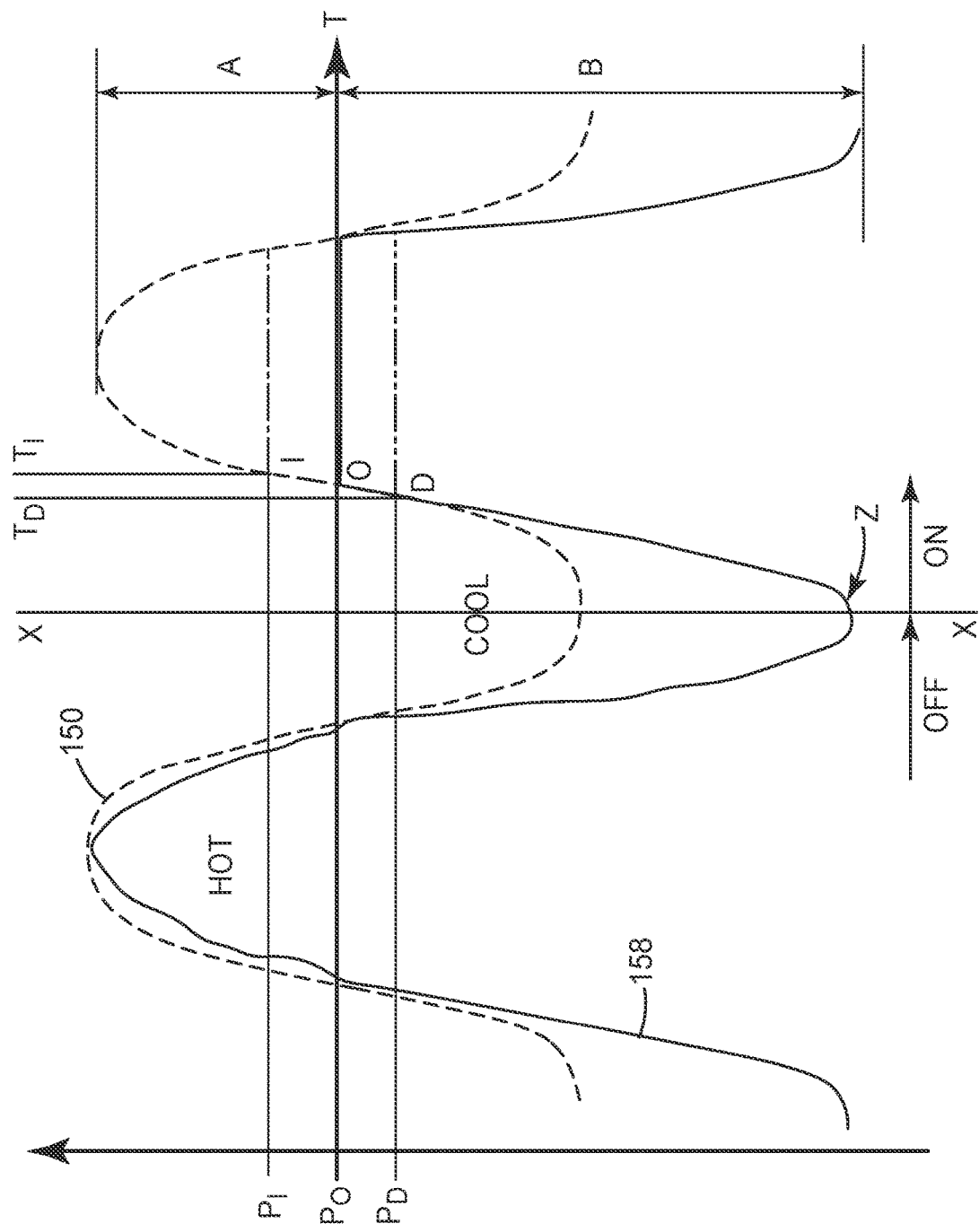
FIG. 9 is a chart illustrating the pressure and flow characteristics of the exhaust apparatus of the present invention.

Turning now to FIG. 9, the chart shows a representation of pressure in, and flow rate through, the filtered air cavity of the exhaust apparatus 10 of the present invention in use with the respirator 120. The dashed line 150 once again represents the flow rate through the mask 100 and the solid line 158 represents the pressure in the mask cavity 140. To the left of the centerline X-X the exhaust apparatus 10 is switched off and to the right it is switched on. With the exhaust apparatus 10 switched off the pressure oscillates about zero subject to the larger maximal negative pressure resulting from the pressure drop across the filters. With the device switched on, the pressure line rises from its low point Z towards zero as the wearer inhales through the filters. As the wearer breaths in through the filter, the controller 28 monitors the rise in pressure in the cavity 140 via the pressure conduit 34. When the controller detects a predetermined pressure in the cavity 140, in this instance Po (equal to zero), the controller 28 controls the motor 20 to initiate the blower 12. This pulls air from the cavity 140 in order to assist the breathing of the wearer. The blower 12 continues to operate until such time as the pressure in the cavity 140 falls below the predetermined Po at which point the controller stops the motor 20.

The extent of exhale breath assist may be varied by decreasing the predetermined pressure, as indicated by $P_D$, or increasing the predetermined pressure, as indicated by $P_1$. $P_D$ delivers a cooler feel to the wearer and $P_1$ a warmer feel. It is conceivable that this variation in cooling effect could be controlled by the wearer in response to the operating conditions.

It will be appreciated that whilst FIG. 9 depicts the same predetermined pressure at the beginning and the end of the exhalation breath, that is to say $P_D$, for example, remains constant throughout the exhalation breath, it is conceivable within the scope of the invention that the blower 12 could be started at a first predetermined pressure and stopped at a second predetermined pressure. In the situation where the first predetermined pressure were greater than the second predetermined pressure, the controller would start the blower momentarily after the initiation of the wearer's exhale breath and stop the blower momentarily after the end of the wearer's exhale breath. In the situation where the second predetermined pressure were greater than the first predetermined pressure, the controller would start the blower momentarily before the initiation of the wearer's exhale breath and stop the blower momentarily before the end of the wearer's exhale breath.

FIG. 9 shows an idealized representation of the pressure plots. In reality the blower is controlled in real time in order to best approximate the desired predetermined pressure value. A number of factors affect this control. Firstly, the pressure drop across the exhale valve will vary from valve to valve. Accordingly the motor may be required to work harder to achieve a predetermined value, say $P_1$, across a narrow exhale valve orifice, than it might across a larger orifice exhale valve.

It will be appreciated that the intention of the invention is to provide an apparatus that provides breath assist only through the wearer's exhale breath. However, dependent on the predetermined pressure to be achieved it will be appreciated from FIG. 9 that the blower might be initiated slightly before the end of the inhale breath at $T_D$ (in order to achieve more fan assistance at predetermined pressure $P_D$) or slightly after at $T_1$ (in order to achieve less fan assistance at predetermined pressure $P_E$). Equally the blower 12 might be stopped slightly after the end of the exhale breath (in order to achieve more fan assistance at predetermined pressure $P_D$) or slightly before (in order to achieve less fan assistance at predetermined pressure $P_E$). Thus the operation of the blower 12 outside of the exhale breath is only for a very short period of time and is a control technique provided to improve the comfort of the wearer. This is entirely in keeping with the desire to avoid driving the motor during the inhale breath, given the clear advantages of providing a control regime which takes into account system hysteresis and improved comfort by operating the blower momentarily during the beginning or end of the inhale breath.

The invention claimed is:

1. A generally L-shaped exhaust apparatus for connection to a personal protection respiratory device that defines a filtered air volume adjacent to the face of a wearer and comprises at least one exhalation valve, the apparatus comprising:
   a housing comprising a rearwardly extending section and an upwardly extending portion;
   a blower in fluid connection with the at least one exhalation valve, the blower being responsive to the wearer's respiratory cycle to draw a substantial portion of the wearer's exhaled breath through the at least one exhalation valve;
   a controller;
   a rechargeable battery to supply power for the apparatus, wherein the rechargeable battery is housed in the rearwardly extending section of the housing, allowing the L-shaped exhaust apparatus' center of mass to sit closely to the wearer's head's center of mass,
   wherein the rechargeable battery is generally perpendicular to the blower within the rearwardly extending section; and a pressure sensor for sensing a pressure generated by the wearer's breathing cycle and sending a pressure signal indicative of the pressure to the controller, wherein, in response to the wearer's respiratory cycle, the blower operates throughout the wearer's exhale breath, or a substantial period thereof, and does not operate throughout the wearer's inhale breath, or a substantial period thereof, and the controller being in communication with the pressure sensor and the blower, wherein the controller operates the blower in response to the pressure signal.

2. The exhaust apparatus of claim 1, wherein the blower, controller, battery, and pressure sensor are contained with the housing.

3. The exhaust apparatus of claim 1, wherein the pressure is sensed in a filtered air volume of the personal protection respiratory device.

4. The exhaust apparatus of claim 1, wherein the pressure is sensed downstream of the exhalation valve or upstream of the inhalation valve.

5. The exhaust apparatus of claim 1, wherein the controller starts the blower when the pressure sensed by the pressure sensor reaches a first predetermined pressure.

6. The exhaust apparatus of claim 5, wherein the controller stops the blower when the pressure sensed by the pressure sensor falls below a second predetermined pressure.

7. The exhaust apparatus of claim 6, wherein the first predetermined pressure and the second predetermined pressure are a common predetermined pressure.

8. The exhaust apparatus of claim 7, wherein the common predetermined pressure is substantially ambient pressure so that the controller starts the blower substantially at the initiation of the wearer's exhale breath and stops the blower substantially at the end of the wearer's exhale breath.

9. The exhaust apparatus of claim 8, wherein the common predetermined pressure is higher than ambient pressure so that the controller starts the blower momentarily after the initiation of the wearer's exhale breath and stops the blower momentarily before the end of the wearer's exhale breath.

10. The exhaust apparatus of claim 7, wherein the common predetermined pressure is lower than ambient pressure so that the controller starts the blower momentarily before the initiation of the wearer's exhale breath and stops the blower momentarily after the end of the wearer's exhale breath.

11. The exhaust apparatus of claim 5, wherein the first predetermined pressure is greater than the second predetermined pressure so that the controller starts the blower momentarily after the initiation of the wearer's exhale breath and stops the blower momentarily after the end of the wearer's exhale breath.

12. The exhaust apparatus of claim 5, wherein the second predetermined pressure is greater than the first predetermined pressure so that the controller starts the blower momentarily before the initiation of the wearer's exhale breath and stops the blower momentarily before the end of the wearer's exhale breath.

13. The exhaust apparatus of claim 1, wherein the blower further comprises an inlet, a motor, a fan, and an outlet.

14. The exhaust apparatus of claim 1, further comprising an attachment for releasably connecting the blower to the at least one exhalation valve.

15. The exhaust apparatus of claim 1, wherein the personal protection respiratory device is selected from a group consisting of disposable, reusable, half mask, full face, particulate, gas and vapor and tight-fitting hood respirators.

16. A method of controlling the exhaust apparatus of claim 1, comprising:
setting a predetermined pressure;
starting the blower when the pressure sensed by the pressure sensor reaches the predetermined pressure; and
stopping the blower when the pressure sensed by the pressure sensor falls below the predetermined pressure.

* * * * *